US009928597B2

(12) United States Patent
Hara et al.

(10) Patent No.: US 9,928,597 B2
(45) Date of Patent: Mar. 27, 2018

(54) IMAGE PROCESSING APPARATUS, IMAGE PROCESSING METHOD AND IMAGE PROCESSING PROGRAM

(71) Applicant: RIGAKU CORPORATION, Tokyo (JP)

(72) Inventors: Yukihiro Hara, Hino-shi (JP);
Takafumi Koike, Setagaya-ku (JP);
Minoru Maesawa, Musashimurayama-shi (JP)

(73) Assignee: RIGAKU CORPORATION, Tokyo (JP)

(*) Notice: Subject to any disclaimer, the term of this patent is extended or adjusted under 35 U.S.C. 154(b) by 151 days.

(21) Appl. No.: 14/822,604

(22) Filed: Aug. 10, 2015

(65) Prior Publication Data
US 2016/0055639 A1 Feb. 25, 2016

(30) Foreign Application Priority Data

Aug. 22, 2014 (JP) ................. 2014-169775

(51) Int. Cl.
*A61B 5/055* (2006.01)
*G06T 7/00* (2017.01)
(Continued)

(52) U.S. Cl.
CPC .......... *G06T 7/0042* (2013.01); *A61B 5/0035* (2013.01); *A61B 5/0071* (2013.01);
(Continued)

(58) Field of Classification Search
None
See application file for complete search history.

(56) References Cited

U.S. PATENT DOCUMENTS 6,522,908 B1* 2/2003 Miyashita ............ A61B 5/0064
600/409
7,912,262 B2 3/2011 Timmer et al.
(Continued)

FOREIGN PATENT DOCUMENTS

JP 2006-320722 A 11/2006
JP 2007-7255 A 1/2007
(Continued)

*Primary Examiner* — Said Broome
(74) *Attorney, Agent, or Firm* — Birch, Stewart, Kolasch & Birch, LLP

(57) ABSTRACT

There are provided an image processing apparatus, an image processing method and an image processing program which can easily and accurately specify and analyze an abnormal part of a subject. An image processing apparatus 100 used to specify the abnormal part of the subject includes a calculation unit 130 calculating position adjustment data between contour data of a specific subject extracted from an X-ray radiographic image and contour data of a photographic image obtained by photographing the specific subject, a sectional image generation unit 140 generating a sectional image of a three-dimensional X-ray CT image correlated with the X-ray radiographic image on a plane parallel with a light receiving face of a two-dimensional biolight image correlated with the photographic image, and a display processing unit 150 displaying the three-dimensional X-ray CT image and the two-dimensional biolight image in superposition on the sectional image, using the calculated position adjustment data.

5 Claims, 18 Drawing Sheets

(51) Int. Cl.

| | | |
|---|---|---|
| *G06K 9/46* | (2006.01) | |
| *G06K 9/52* | (2006.01) | |
| *G06K 9/62* | (2006.01) | |
| *G06T 3/40* | (2006.01) | |
| *G06T 11/60* | (2006.01) | |
| *G06T 15/00* | (2011.01) | |
| *A61B 6/03* | (2006.01) | |
| *A61B 5/00* | (2006.01) | |
| *G06T 15/08* | (2011.01) | |
| *G06T 19/00* | (2011.01) | |
| *G06T 7/33* | (2017.01) | |
| *A61B 6/00* | (2006.01) | |

(52) U.S. Cl.
CPC ............ *A61B 5/7425* (2013.01); *A61B 6/032* (2013.01); *A61B 6/5247* (2013.01); *G06K 9/4604* (2013.01); *G06K 9/52* (2013.01); *G06K 9/6201* (2013.01); *G06T 3/40* (2013.01); *G06T 7/0012* (2013.01); *G06T 7/0014* (2013.01); *G06T 7/33* (2017.01); *G06T 11/60* (2013.01); *G06T 15/005* (2013.01); *G06T 15/08* (2013.01); *G06T 19/00* (2013.01); *A61B 5/055* (2013.01); *A61B 6/508* (2013.01); *G06T 2200/24* (2013.01); *G06T 2207/10081* (2013.01); *G06T 2207/10116* (2013.01); *G06T 2207/30096* (2013.01); *G06T 2210/41* (2013.01); *G06T 2219/028* (2013.01)

(56) References Cited

U.S. PATENT DOCUMENTS

| | | | |
|---|---|---|---|
| 2002/0035458 A1* | 3/2002 | Kim | G06T 15/00 |
| | | | 703/6 |
| 2003/0169847 A1* | 9/2003 | Karellas | A61B 6/481 |
| | | | 378/98.3 |
| 2004/0263535 A1 | 12/2004 | Birkenbach et al. | |
| 2006/0262118 A1 | 11/2006 | Barfuss et al. | |
| 2008/0192996 A1 | 8/2008 | Timmer et al. | |
| 2009/0034684 A1 | 2/2009 | Bernard et al. | |
| 2012/0176406 A1* | 7/2012 | Elenbaas | A61B 6/032 |
| | | | 345/629 |
| 2012/0321033 A1 | 12/2012 | Stearns et al. | |
| 2013/0279646 A1 | 10/2013 | Koike et al. | |
| 2016/0228079 A1 | 8/2016 | Stearns et al. | |

FOREIGN PATENT DOCUMENTS

| | | |
|---|---|---|
| JP | 2007-159769 A | 6/2007 |
| JP | 2008-532612 A | 8/2008 |
| JP | 2009-34503 A | 2/2009 |
| JP | 2010-032338 A | 2/2010 |
| JP | 2013-223643 A | 10/2013 |
| JP | 2014-519953 A | 8/2014 |

* cited by examiner

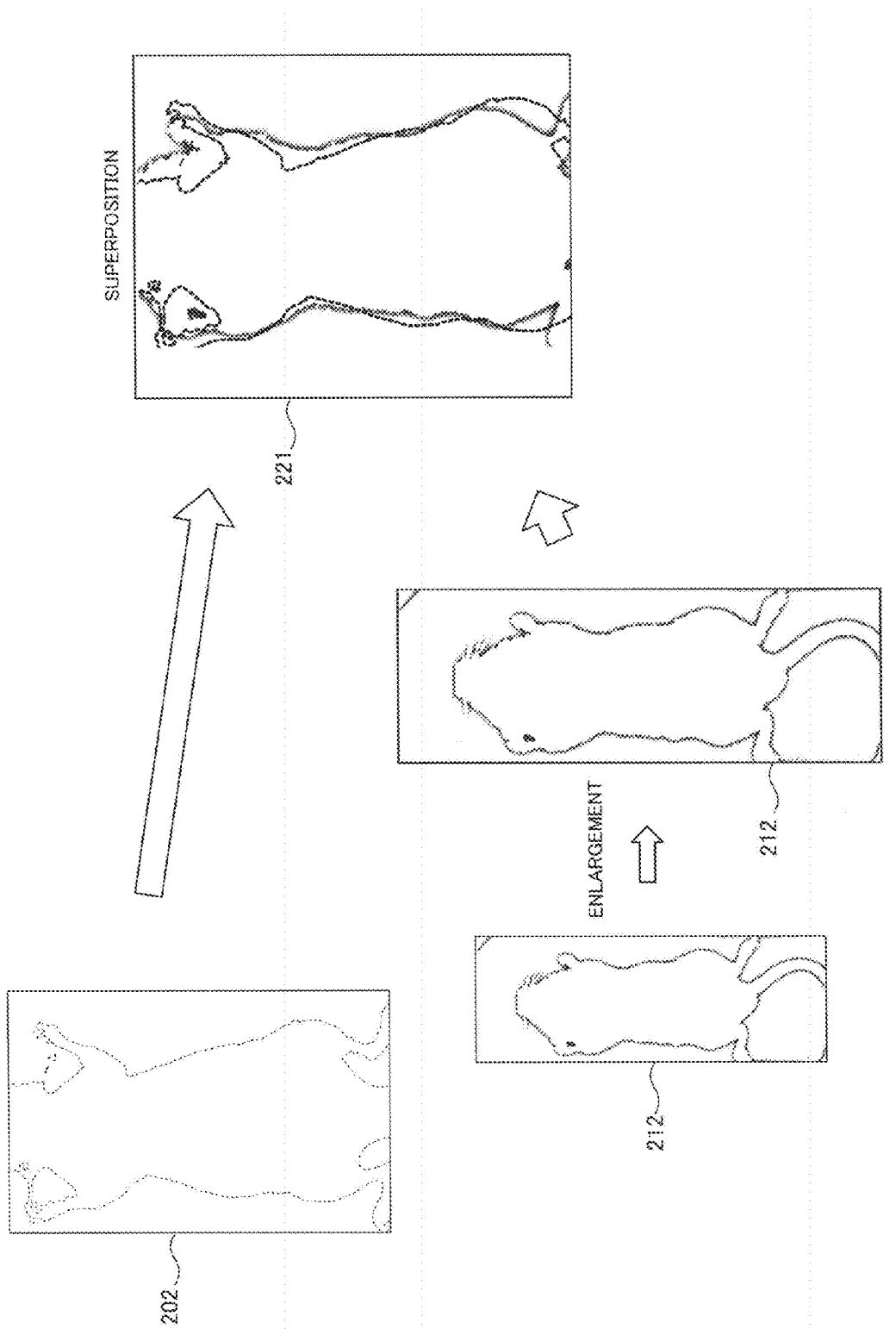

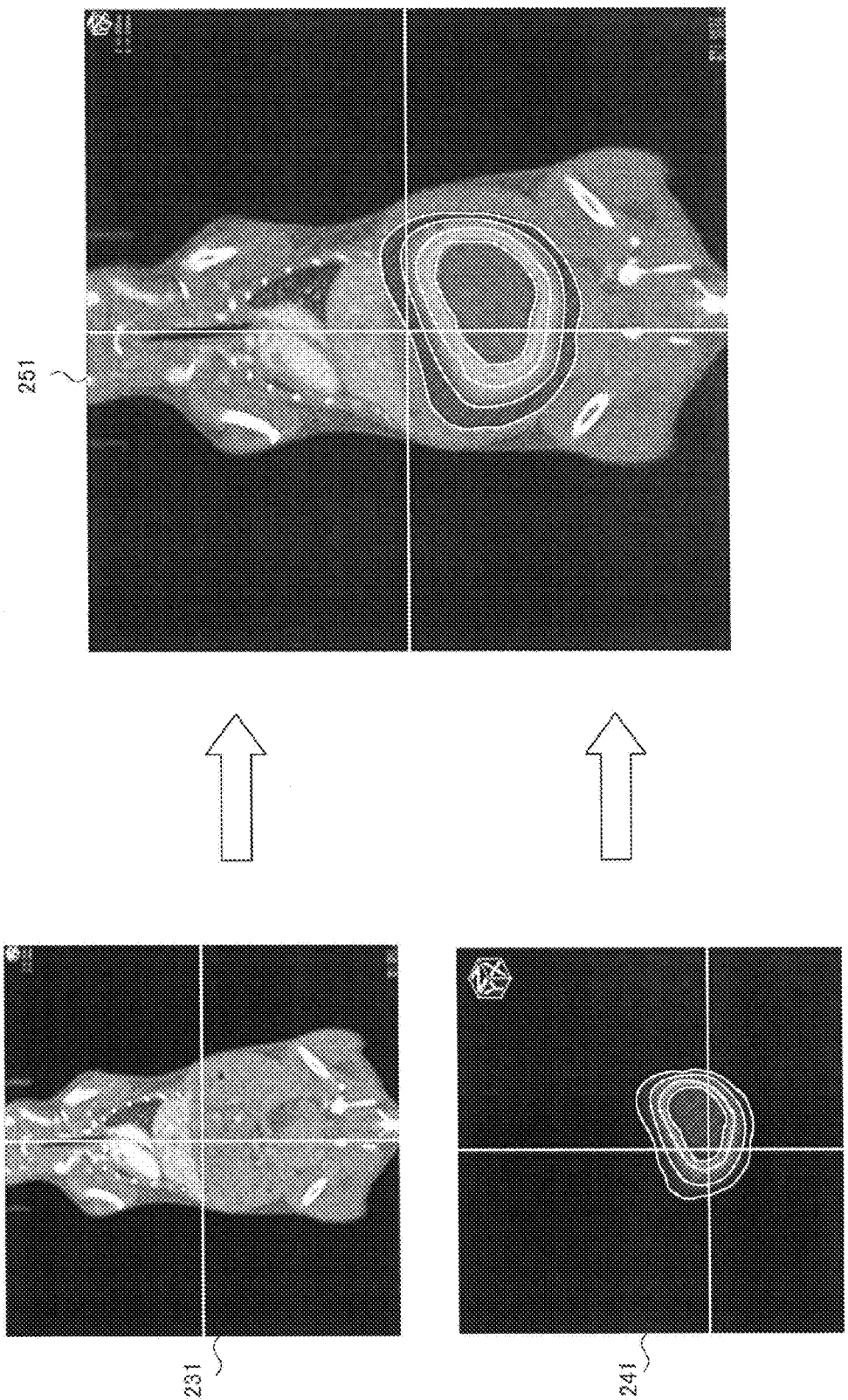

IMAGE PROCESSING APPARATUS, IMAGE PROCESSING METHOD AND IMAGE PROCESSING PROGRAM

FIELD OF THE INVENTION

The present invention relates to an image processing apparatus, an image processing method and an image processing program used to specify an abnormal part of a subject.

DESCRIPTION OF THE RELATED ART

Recently, an imaging technology targeting on a living body has progressed and it has become possible to acquire an image by performing in-vivo scanning on an experimental animal such as a mouse and a rat in real time and to specify and analyze a lesion part of the experimental animal. In particular, development of in-vivo imaging using a living experimental animal is in progress as an important technology.

X-ray CT scanning is effective for in-vivo observation of the experimental animal. In the X-ray CT scanning, a method of capturing a plurality of pieces of radiographic image data by rotating a measurement system relative to a subject and reconfiguring a three-dimensional CT image from the plurality of pieces of captured radiographic image data is known (for example, Patent Document 1).

On the other hand, in order to specify and observe the lesion part in the body of the experimental animal, fluorescence imaging is effective. The fluorescence imaging is a technology of integrating a fluorescent-labeled probe on an in-vivo target part and monitoring the dynamic phase of the probe from the outside of the body, and a method of detecting the concentration of a fluorescent reagent via an optical microscope is known as the fluorescence imaging (for example, Patent Document 2).

Then, a technology of tying up the X-ray CT scanning with the fluorescence imaging as described above is studied and proposed. For example, a device described in Patent Document 3 displays an X-ray transmission image used for forming an X-ray CT scanning plan and a corresponding RI distribution image in superposition so as to make precise formation of the X-ray CT scanning plan by an operator possible.

In addition, an image processing system described in Patent Document 4 mutually matches positions of a two-dimensional fluorescent image and a three-dimensional MR/CT image as a fused or composite image and displays the fused or composite image. As a result, it is made possible to display raw two-dimensional image data which has been captured in regard to the body volume in correlation with three-dimensional volume data obtained by another system.

In addition, in a system described in Patent Document 5, a system for micro X-ray tomography is integrated with a system for optical imaging. Thereby, radiographing of a plurality of kinds of images is made possible without moving the subject between separate systems.

PATENT DOCUMENT

[Patent Document 1] Japanese Unexamined Patent Application Publication No. 2013-223643

[Patent Document 2] Japanese Unexamined Patent Application Publication No. 2010-032338

[Patent Document 3] Japanese Unexamined Patent Application Publication No. 2007-159769

[Patent Document 4] Japanese Unexamined Patent Application Publication No. 2008-532612

[Patent Document 5] U.S. Unexamined Patent Application Publication No. 2012/0321033

However, in the above-mentioned technologies of fusing the X-ray CT scanning with the fluorescence imaging, a burden-imposing processing procedure is applied and it is difficult to easily and accurately specify and analyze the abnormal part of the subject. For example, in the system described in Japanese Unexamined Patent Application Publication No. 2008-532612, the position of the two-dimensional image data is matched first with that of the three-dimensional image data. This means that processing which would not be so easy is performed.

SUMMARY OF THE INVENTION

The present invention has been made in view of the above-mentioned circumstances and aims to provide an image processing apparatus, an image processing method and an image processing program making it possible to display a three-dimensional X-ray CT image and a two-dimensional fluorescent image by automatically superposing these images on a sectional image of a subject and thereby making it possible to easily and accurately specify and analyze the abnormal part of the subject.

(1) In order to attain the above object, according to one embodiment of the present invention, there is provided an image processing apparatus which is used to specify the abnormal part of the subject and includes a calculation unit configured to calculate position adjustment data used for matching between contour data of a specific subject which have been extracted from an X-ray radiographic image and contour data of a photographic image obtained by photographing the specific subject and a display processing unit configured to display a three-dimensional X-ray CT image which has been correlated with the X-ray radiographic image and a two-dimensional biolight image which has been correlated with the photographic image in superposition by using the calculated position adjustment data.

Thereby, it is possible to display the three-dimensional X-ray CT image and the two-dimensional biolight image by automatically superposing these images on the sectional image of the subject and thereby easy and accurate specification and analysis of the abnormal part of the subject become possible.

(2) The image processing apparatus according to one embodiment of the present invention further includes a sectional image generation unit configured to generate a sectional image of the three-dimensional X-ray CT image on a plane which is parallel with a light receiving face of the two-dimensional biolight image. Thereby, it is possible to display the sectional image of the three-dimensional X-ray CT image and to more accurately specify a lesion part (the abnormal part) by applying a maximum intensity projection method.

(3) In addition, in the image processing apparatus according one embodiment of the present invention, the sectional image generation unit generates the sectional image of the three-dimensional X-ray CT image by applying the maximum intensity projection method to the three-dimensional X-ray CT image within a predetermined range in a direction vertical to the light receiving face of the two-dimensional biolight image. Thereby, since it is possible to display the sectional image of the three-dimensional X-ray CT image to which the maximum intensity projection method has been automatically applied, it is possible to accurately specify the abnormal part of the subject.

(4) In addition, the image processing apparatus according to one embodiment of the present invention further includes an operation reception unit configured to receive an operation of specifying a range on the sectional image from a user and the sectional image generation unit generates the sectional image of the three-dimensional X-ray CT image by applying the maximum intensity projection method to the three-dimensional X-ray CT image for the specified range in the direction vertical to the light receiving face of the two-dimensional biolight image. Thereby, when there exists the plurality of lesion parts, it becomes easy for the user to specify the lesion parts by a simple operation by locally using the maximum intensity projection method for the three-dimensional X-ray CT image as necessary and thereby it is possible to improve convenience.

(5) In addition, in the image processing apparatus according to one embodiment of the present invention, the calculation unit calculates a rate of magnification from a ratio in pixel size between the X-ray radiographic image and the photographic image as the position adjustment data between the contour data. Thereby, it is possible to accurately calculate the rate of magnification as the position adjustment data between the contour data.

(6) In addition, in the image processing apparatus according to one embodiment of the present invention, the calculation unit adjusts the size between the contour data by using the rate of magnification and thereafter calculates relative positions on a plane and an angle of rotation around a specific axis of the X-ray radiographic image and the photographic image, as the position adjustment data between the contour data such that a correlation value between the contour data satisfies a predetermined condition. Thereby, it is possible to calculate the reasonable relative positions on the plane and the reasonable angle of rotation around the specific axis of the X-ray radiographic image and the photographic image, as the position adjustment data between the contour data.

(7) According to another embodiment of the present invention, there is provided an image processing method which is executed by a computer and used to specify an abnormal part of a test subject. The image processing method includes the steps of calculating position adjustment data between contour data of a specific subject which have been extracted from an X-ray radiographic image and contour data of a photographic image obtained by photographing the specific subject and displaying a three-dimensional X-ray CT image which has been correlated with the X-ray radiographic image and a two-dimensional biolight image which has been correlated with the photographic image in superposition by using the calculated position adjustment data. Thereby, easy and accurate specification and analysis of the abnormal part of the subject become possible.

(8) In addition, according to further another embodiment of the present invention, there is provided an image processing program which is used to specify an abnormal part of a subject and causes a computer to execute a series of processing including the processes of calculating position adjustment data between contour data of a specific subject which have been extracted from an X-ray radiographic image and contour data of a photographic image obtained by photographing the specific subject and displaying a three-dimensional X-ray CT image which has been correlated with the X-ray radiographic image and a two-dimensional biolight image which has been correlated with the photographic image in superposition by using the calculated position adjustment data. Thereby, easy and accurate specification and analysis of the abnormal part of the subject become possible.

According to the embodiments of the present invention, it is possible to display the three-dimensional X-ray CT image and the two-dimensional biolight image by automatically superposing these images on the sectional image of the subject and easy and accurate specification and analysis of the abnormal part of the subject become possible.

BRIEF DESCRIPTION OF THE DRAWINGS

FIG. 7 is a diagram illustrating a procedure of mutually superposing images the contour of each of which has been extracted.

FIG. 8 is a diagram illustrating a process of mutually superposing a CT image and a fluorescent image.

DETAILED DESCRIPTION OF THE INVENTION

Figure 1:
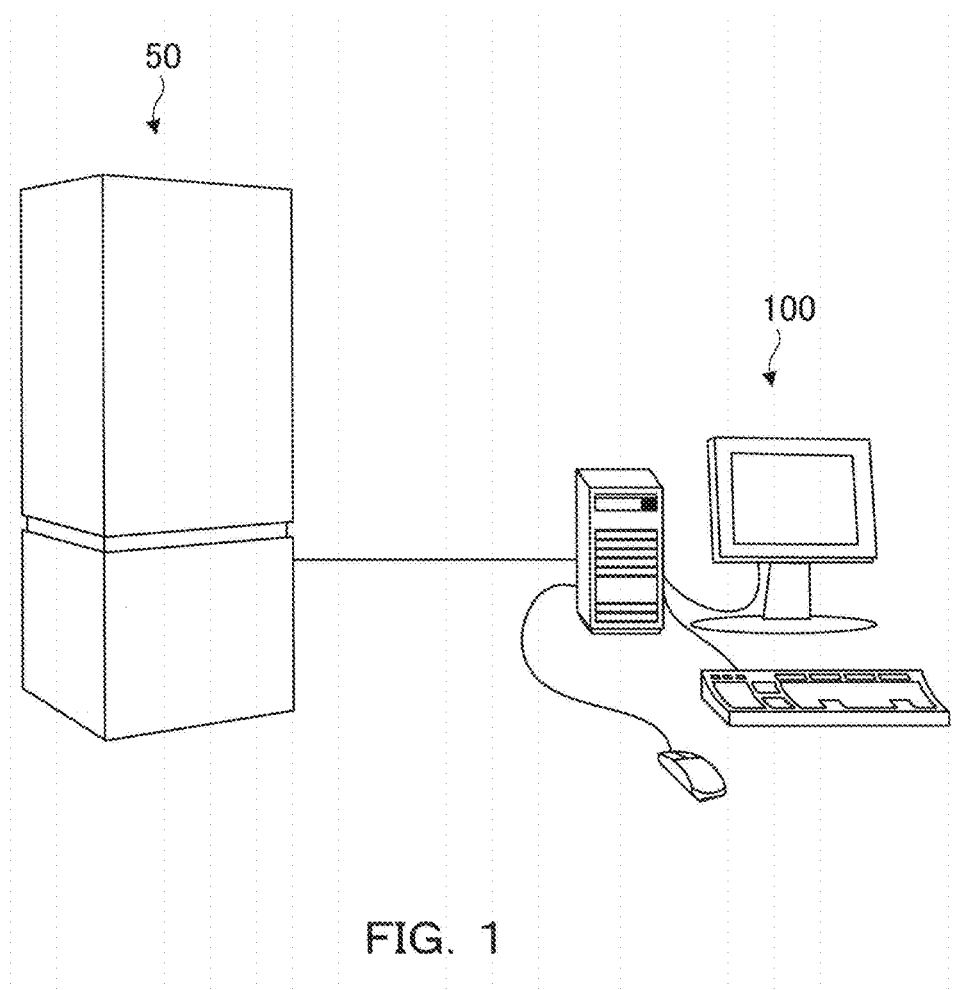
FIG. 1 is a schematic diagram illustrating a measurement apparatus and an image processing apparatus of the present invention.

Next, preferred embodiments of the present invention will be described with reference to the drawings. For facilitating understanding of description, the same reference numerals are assigned to the same configurations in each drawing and repetitive description is omitted.

First Embodiment (System Configuration by Measurement Apparatus and Image Processing Apparatus)

FIG. 1 is a schematic diagram illustrating a measurement apparatus 50 and an image processing apparatus 100. The measurement apparatus 50 is capable of performing X-ray CT scanning and fluorescence imaging (biolight imaging) on a subject M (a specific subject). It is possible to subject an X-ray CT image and a biolight image which have been photographed by the measurement apparatus 50 to image processing by the image processing apparatus 100 and to display the images in the integrated form. Incidentally, the biolight imaging includes fluorescence imaging and luminescence imaging.

(Configuration of Measurement Apparatus)

Figure 2A:
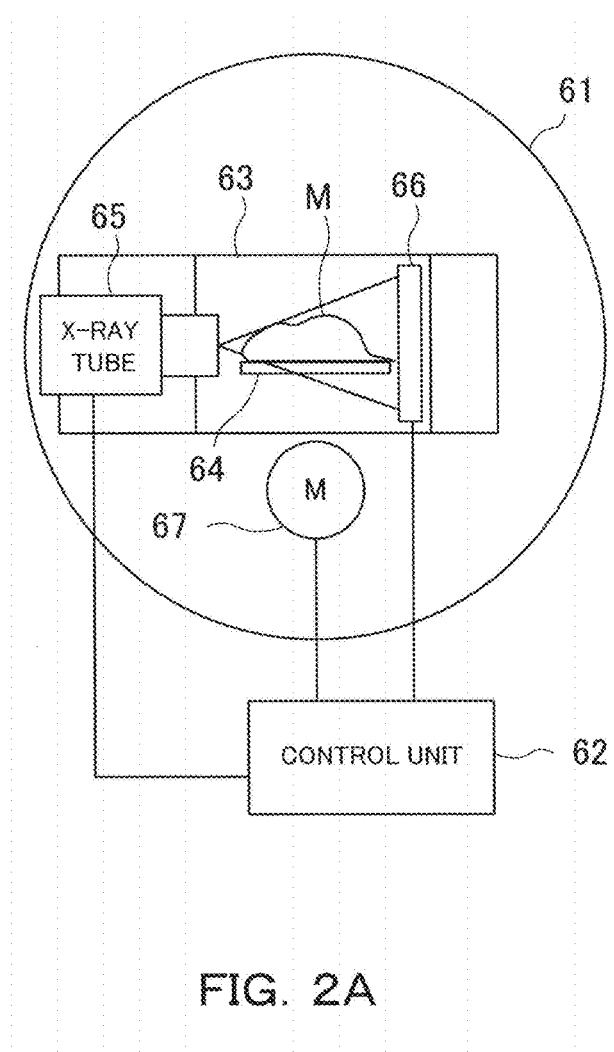
FIG. 2A is a schematic diagram illustrating a configuration for X-ray CT scan of the measurement apparatus.
Figure 2B:
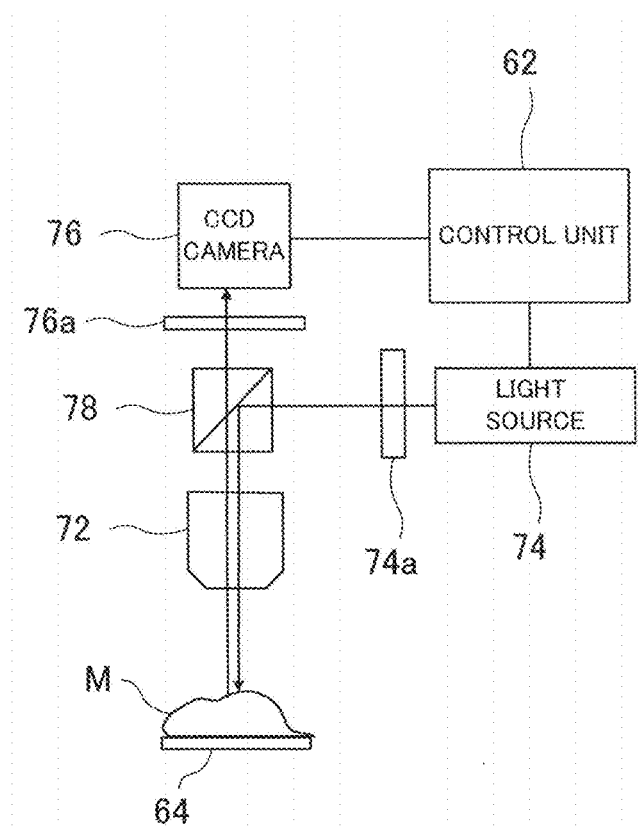
FIG. 2B is a schematic diagram illustrating a configuration for fluorescence imaging of the measurement apparatus.

FIG. 2A and FIG. 2B are schematic diagrams respectively illustrating a configuration for X-ray CT scanning and a configuration for fluorescence imaging of the measurement apparatus. FIG. 2A illustrates the configuration for capturing the X-ray CT image of the subject M in the measurement apparatus 50. The measurement apparatus 50 includes a gantry 61 and a control unit 62 as the configuration for X-ray CT scanning. The gantry 61 includes a rotating arm 63, a stage 64, an X-ray tube 65, a two-dimensional detector 66 and an arm rotation motor 67.

The X-ray tube 65 and the two-dimensional detector 66 are fixed to the rotating arm 63 so as to mutually face centering on the subject M to be held on the stage 64. The rotating arm 63 is installed in the gantry 61 so as to be rotatable relative to the subject M.

The X-ray tube 65 radiates X-rays to be shaped into a cone beam, the subject M is irradiated with the X-rays and the two-dimensional detector 66 detects the X-rays which have passed through the subject M. The two-dimensional detector 66 includes a detection face which detects the X-rays and detects the X-rays which pass through the subject M as radiographic image data. The arm rotation motor 67 rotates the rotating arm 63 and thereby rotates the entire of the gantry 61 continuously. It becomes possible for the measurement apparatus 50 to detect X-ray radiographic image data in this way.

FIG. 2B is a diagram illustrating the configuration for photographing a fluorescent image of the subject M in the measurement apparatus 50. As illustrated in FIG. 2B, the measurement apparatus 50 includes an objective lens system 72, a light source 74, filters 74a and 76a, a CCD camera 76 and a dichroic mirror 78 as the configuration for photographing by fluorescence imaging. Owing to such a configuration, photographing by fluorescence imaging of the subject M with the probe imbedded becomes possible.

The light source 74 irradiates excitation light or illumination light and the dichroic mirror 78 reflects the irradiation light. The objective lens system 72 condenses reflected light upon an observation part of the subject M. Then, the objective lens system 72 condenses fluorescence generated from the probe in the observation part and the CCD camera 76 receives the fluorescence transmitted through the dichroic mirror 78 by a light receiving face and generates the fluorescent image of the subject M.

The filters 74a and 76a which selectively transmit light of specific wavelengths are respectively arranged on an optical path of the excitation light from the light source 74 and an optical path of detection light from a sample to the CCD camera 76. The control unit 62 controls operations of the light source 74 and the CCD camera 76 and processes the image taken by the CCD camera 76. It becomes possible for the measurement apparatus 50 to photograph the two-dimensional fluorescent image in this way. In addition, it is also possible for the measurement apparatus 50 to take the photographic image from the same angle as that when photographing the two-dimensional image by biolight imaging without using the excitation light and so forth. Then, pieces of image data on the X-ray radiographic image, the photographic image and the two-dimensional fluorescent image taken by the measurement apparatus 50 are sent to the image processing apparatus 100, are appropriately processed by the image processing apparatus 100 and are accumulated.

(Configuration of Image Processing Apparatus)

Figure 3:
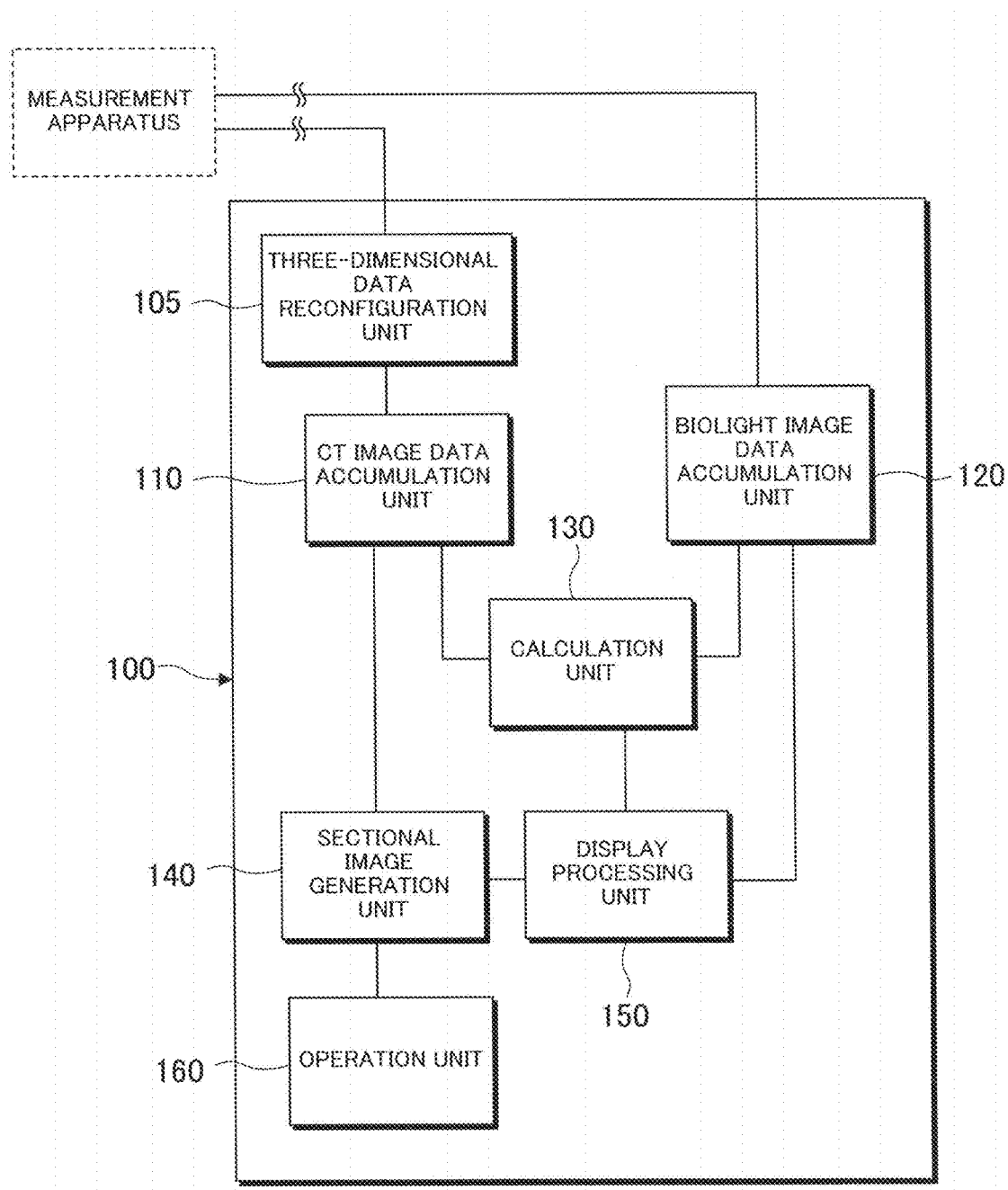
FIG. 3 is a block diagram illustrating a functional configuration of the image processing apparatus of the present invention.

FIG. 3 is a block diagram illustrating a functional configuration of the image processing apparatus 100. The image processing apparatus 100 is used, in particular, for specification of the abnormal part (for example, the lesion part) of the subject and includes a three-dimensional data reconfiguration unit 105, a CT image data accumulation unit 110, a biolight image data accumulation unit 120, a calculation unit 130, a sectional image generation unit 140, a display processing unit 150 and an operation unit 160.

The three-dimensional data reconfiguration unit 105 reconfigures three-dimensional X-ray CT image data from X-ray radiographic image data which has been captured by the measurement apparatus 50. The CT image data accumulation unit 110 accumulates the X-ray radiographic image data which has been captured by the measurement apparatus 50 and the three-dimensional X-ray CT image data obtained by performing reconfiguration processing. As a series of pieces of photographic data for a specific subject, the X-ray radiographic image data and the three-dimensional X-ray CT image data are made to correspond to each other.

The biolight image data accumulation unit 120 accumulates photographic image data and two-dimensional biolight image data photographed by the measurement apparatus 50. Incidentally, the biolight image includes both of the fluorescent image and a luminescence image. As a series of pieces of photographic data for the specific subject, the photographic image data and the two-dimensional biolight image data are made to correspond to each other.

The calculation unit 130 calculates position adjustment data between contour data of the specific subject which have been respectively extracted from the X-ray radiographic image and the photographic image obtained by photographing the specific subject. The position adjustment data include a rate of magnification of one contour image to the other contour image, relative positions on a plane and an angle of rotation around a specific axis of the X-ray radiographic image and the photographic image.

The calculation unit 130 calculates the rate of magnification as the position adjustment data between the contour data from a ratio in pixel size between the X-ray radiographic image and the photographic image. Thereby, it is possible to accurately calculate the rate of magnification between the contour data.

Then, after the size between the contour data has been adjusted by using the rate of magnification, the calculation unit 130 calculates a correlation value between each contour data while changing the relative positions on the plane and the angle of rotation around the specific axis of the X-ray radiographic image and the photographic image. Then, the calculation unit 130 calculates the relative positions on the plane and the angle of rotation around the specific axis of the X-ray radiographic image and the photographic image, as the position adjustment data between the contour data such that the correlation value between the contour data satisfies a predetermined condition. Thereby, it is possible to calculate the reasonable relative positions on the plane and the reasonable angel of rotation around the specific axis of the X-ray radiographic image and the photographic image, as the position adjustment data between the contour data Incidentally, the predetermined condition includes, for example, a condition that the correlation value is the highest, or the correlation value is at least a predetermined value.

The sectional image generation unit 140 generates the sectional image of the three-dimensional X-ray CT image which has been correlated with the X-ray radiographic image on a plane (for example, a coronal plane of the subject) which is parallel with a light receiving face of the two-dimensional biolight image which has been correlated with the photographic image.

In addition, it is preferable for the sectional image generation unit 140 to generate the sectional image of the three-dimensional X-ray CT image by applying a maximum intensity projection method to the three-dimensional X-ray CT image for a designated range in a direction vertical to the light receiving face of the two-dimensional biolight image. Thereby, when there exists the plurality of lesion parts, it is possible for the user to easily specify the lesion parts by the simple operation by locally using the maximum intensity projection method for the three-dimensional X-ray CT image as necessary and, thereby, it is possible to improve convenience.

The display processing unit 150 displays the three-dimensional X-ray CT image and the two-dimensional biolight image in superposition on the sectional image by using the calculated position adjustment data. Thereby, it is possible to display the images by automatically superposing the two-dimensional biolight image on the sectional image which has been obtained from the three-dimensional X-ray CT image of the subject.

The operation unit 160 receives an operation of designating a range on the sectional image from the user. The operation unit 160 is a pointing device such as, for example, a mouse. It becomes possible to designate the range by drawing a circle or a square on the sectional image by the operation unit 160.

(Operation of Image Processing Apparatus)

Figure 4:
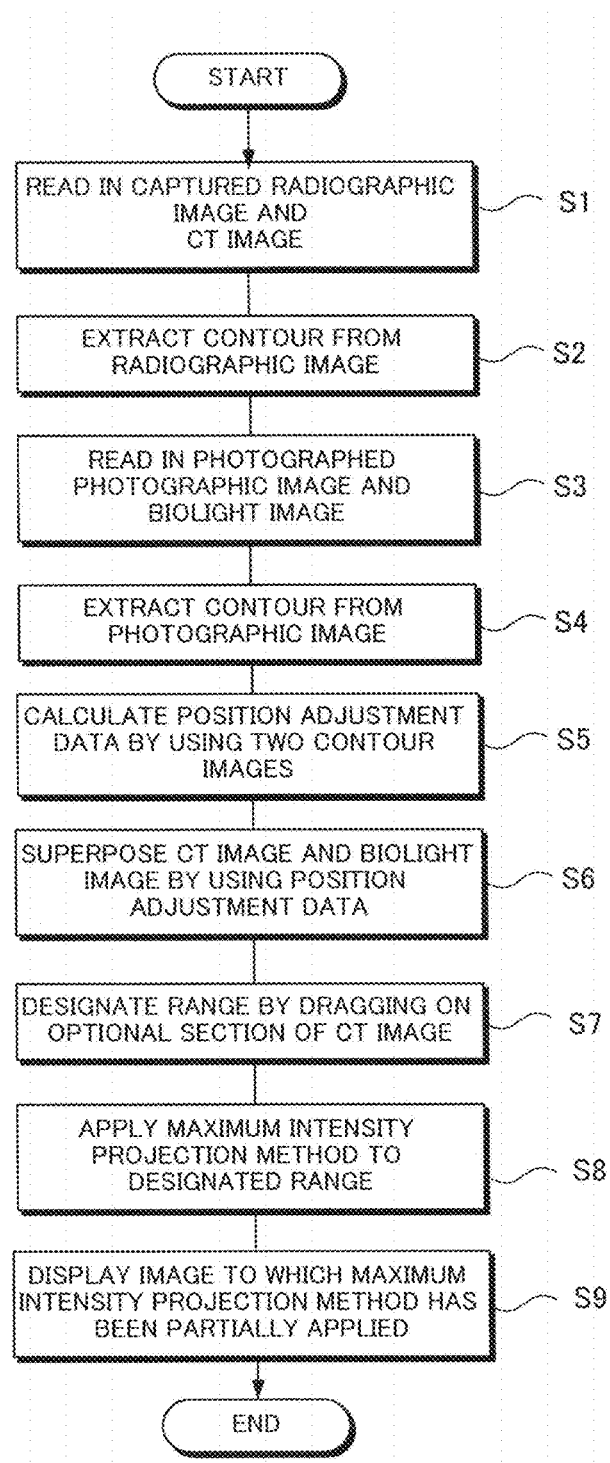
FIG. 4 is a flowchart illustrating one example of an operation of the image processing apparatus according to a first embodiment of the present invention.

FIG. 4 is a flowchart illustrating one example of an operation of the image processing apparatus 100. First, the image processing apparatus 100 reads in the radiographic image data and the three-dimensional X-ray CT image data which have already been captured (step S1). Then, the image processing apparatus 100 extracts the contour of the subject from the read-in radiographic image data (step S2). On the other hand, the image processing apparatus 100 reads in the photographic image data and the two-dimensional biolight image data which have already been photographed (step S3) and then extracts the contour of the subject from the photographic image data (step S4).

Next, the image processing apparatus 100 calculates the position adjustment data using these two contour images (step S5) and then mutually superposes the three-dimensional X-ray CT image data and the two-dimensional biolight image data by using the position adjustment data (step S6).

The image processing apparatus 100 receives range designation by dragging performed by the user on an optional sectional image of image data obtained by mutually superposing the three-dimensional X-ray CT image data and the two-dimensional biolight image data (step S7) and applies the maximum intensity projection method to the designated range (step S8). Consequently, the image processing apparatus 100 displays the sectional image which has been obtained by locally applying the maximum intensity projection method (step S9). It becomes easy to specify the lesion part of the subject in this way. Details of respective processes in such an operation will be described hereinafter.

(Generation of Each Contour Image)

Figure 5A:
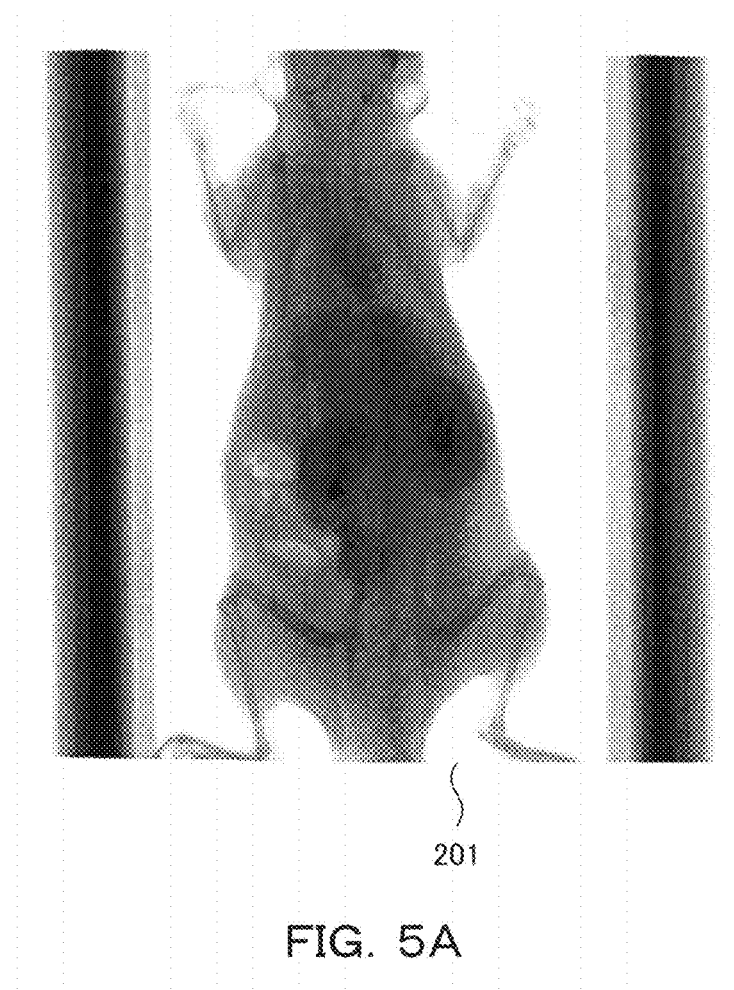
FIG. 5A is a diagram illustrating a radiographic image.
Figure 5B:
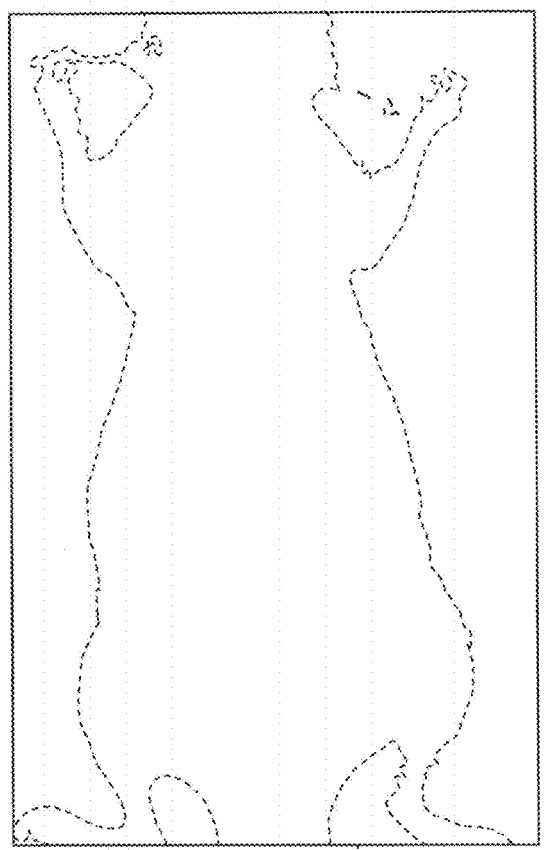
FIG. 5B is a diagram illustrating the image the contour of which has been extracted.

FIG. 5A and FIG. 5B are diagrams respectively illustrating a radiographic image and an image in which the contour has been extracted. A radiographic image 201 illustrated in FIG. 5A is obtained by radiographing a mouse which is the subject from a fixed direction (zero degrees). Then, a contour image 202 illustrated in FIG. 5B is obtained by extracting the contour of the mouse from the radiographic image 201.

Figure 6A:
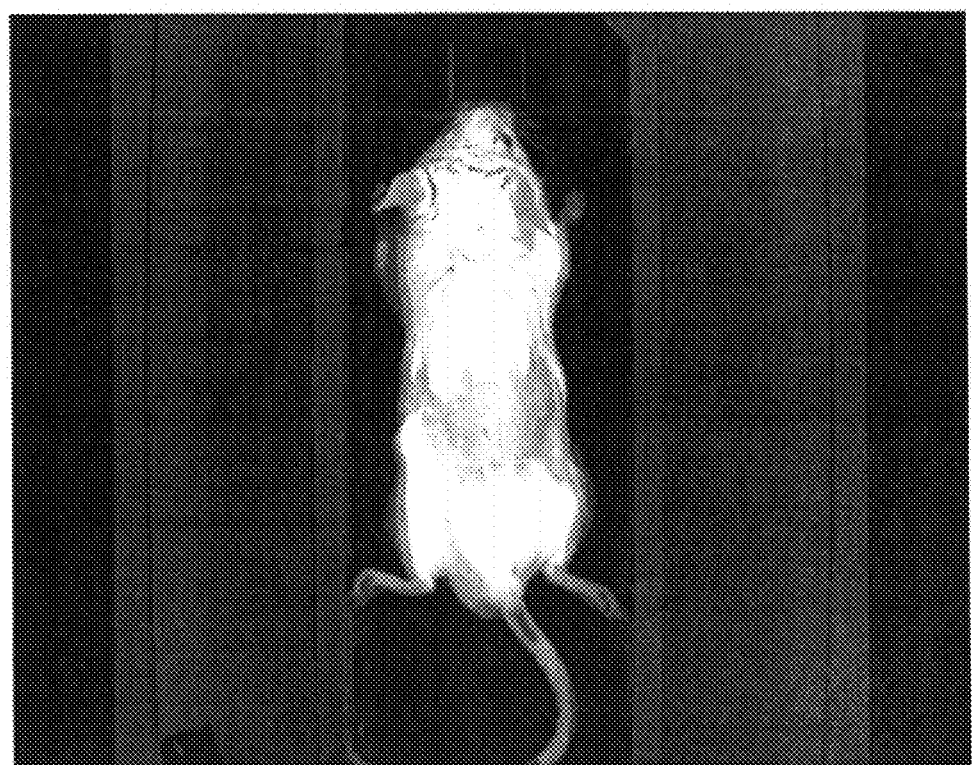
FIG. 6A is a diagram illustrating a photographic image.
Figure 6B:
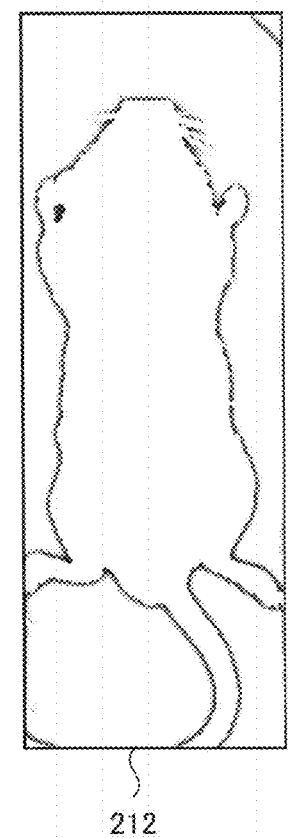
FIG. 6B is a diagram illustrating the image the contour of which has been extracted.

FIG. 6A and FIG. 6B are diagrams respectively illustrating a photographic image and an image in which the contour has been extracted. The photographic image 211 illustrated in FIG. 6A is obtained by photographing the mouse which is the subject from a predetermined direction (=a photographing direction of the photographic image). Then, the contour image 212 illustrated in FIG. 6B is obtained by extracting the contour of the mouse from the photographic image 211.

(Calculation of Position Adjustment Data)

FIG. 7 is a diagram illustrating a procedure of mutually superposing the images in each of which the contour has been extracted. First, the size of each contour image is adjusted. In the example in FIG. 7, since the contour image 212 which has been extracted from the photographic image is smaller than the contour image 202 which has been extracted from the radiographic image, the contour images 212 is adjusted so as to have the size with which mutual superposition of the contour image 212 and the contour image 202 is possible. Specifically, the rate of magnification is obtained from the ratio between the pixel size of the X-ray radiographic image and the pixel size of the photographic image.

After enlargement processing has been performed on the contour image 212, in preparation for superposition, a combination with which the correlation value between the contour data becomes the highest is calculated by changing the relative positions on the plane and the angle of rotation around the specific axis. The relative positions on the plane and the angle of rotation around the specific axis which have been obtained in this way are the position adjustment data between the contour data. For example, in a case where it is necessary to perform adjustment of x: +3.5, y: −12.5 and the rate of magnification of 112% on the two-dimensional fluorescent image for superposition, these numerical values are used as the position adjustment data.

(Superposition)

FIG. 8 is a diagram illustrating a process of mutually superposing a CT image and a two-dimensional fluorescent image. It is possible to obtain a sectional image 251 by mutually superposing a three-dimensional X-ray CT image data 231 and a two-dimensional fluorescent image data 241 by using the position adjustment data obtained as mentioned above.

Second Embodiment

In the above-mentioned embodiment, the user designates the range on the optional section of the image obtained by mutually superposing the three-dimensional X-ray CT image and the two-dimensional biolight image and the maximum intensity projection method is applied. Alternatively, the maximum intensity projection method may be automatically applied, in advance, to the three-dimensional X-ray CT image for the predetermined range so as to present the section along which it is possible to specify the abnormal part of the subject with some accuracy to the user from the first.

In the present embodiment, the sectional image generation unit 140 generates the sectional image of the three-dimensional X-ray CT image by applying the maximum intensity projection method to the three-dimensional X-ray CT image within the predetermined range in the direction vertical to the light receiving face of the two-dimensional biolight image. Thereby, it is possible to display the sectional image of the three-dimensional X-ray CT image to which the maximum intensity projection method has been automatically applied, and thus it is possible to easily and accurately specify the abnormal part of the subject.

(Maximum Intensity Projection Method)

Figure 9A:
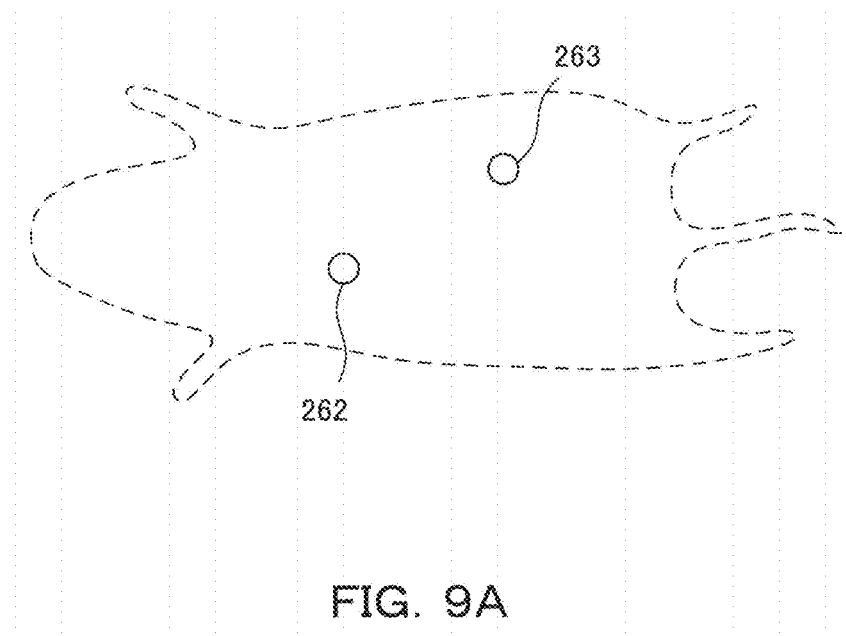
FIG. 9A is a diagram illustrating a coronal plane of a biolight image.
Figure 9B:
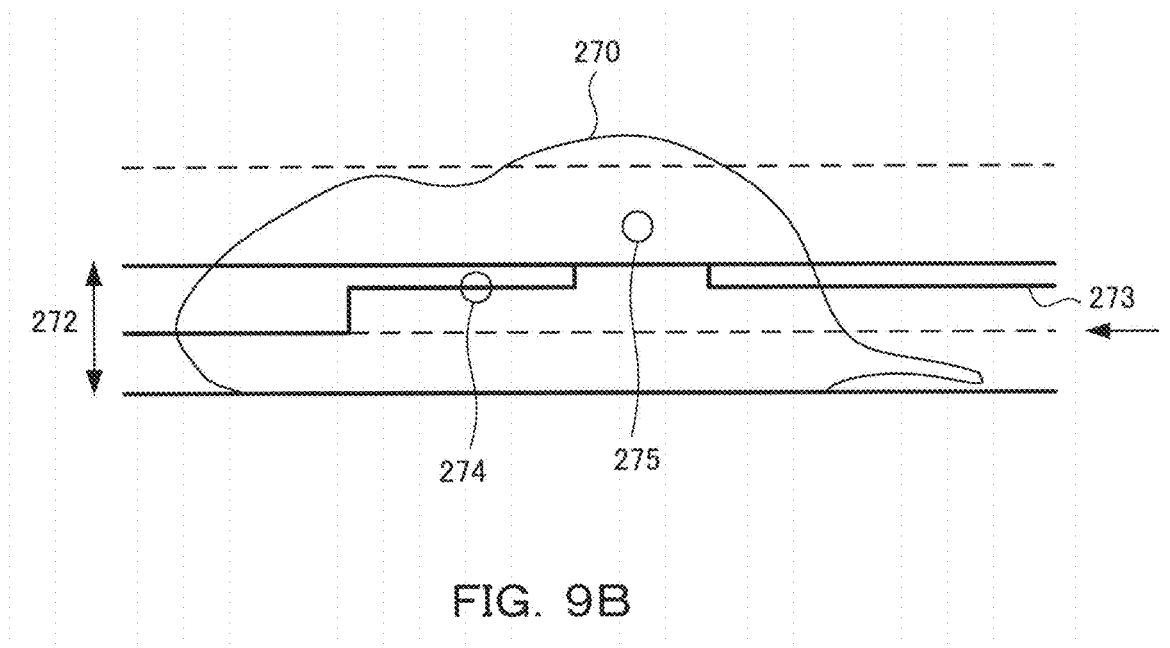
FIG. 9B is a diagram illustrating a sagittal plane of a superposed image which has been subjected to maximum intensity projection.
Figure 9C:
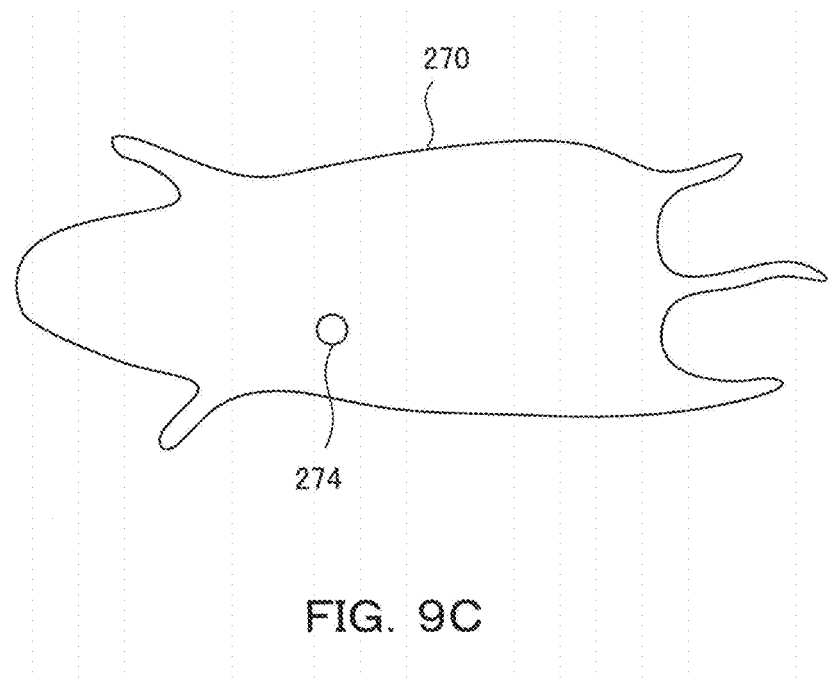
FIG. 9C is a diagram illustrating a coronal section of the image.

FIG. 9A to FIG. 9C are diagrams respectively illustrating a coronal plane of the two-dimensional biolight image, a sagittal plane and a coronal section of an image which has been subjected to maximum intensity projection. In FIG. 9A, fluorescent parts 262 and 263 are displayed in the subject. The sagittal plane diagram illustrated in FIG. 9B illustrates that the coronal section diagram illustrated in FIG. 9C is obtained by projecting a section 273 which takes a maximum intensity within a predetermined range 272 of a subject 270 viewed from the sagittal plane. In a case where abnormal parts 274 and 275 are present in the subject 270, when the image is displayed along the section 273 by applying the maximum intensity projection method in the range 272, the abnormal part 275 is not detected. Therefore, further local application of the maximum intensity projection method becomes effective.

Figure 10:
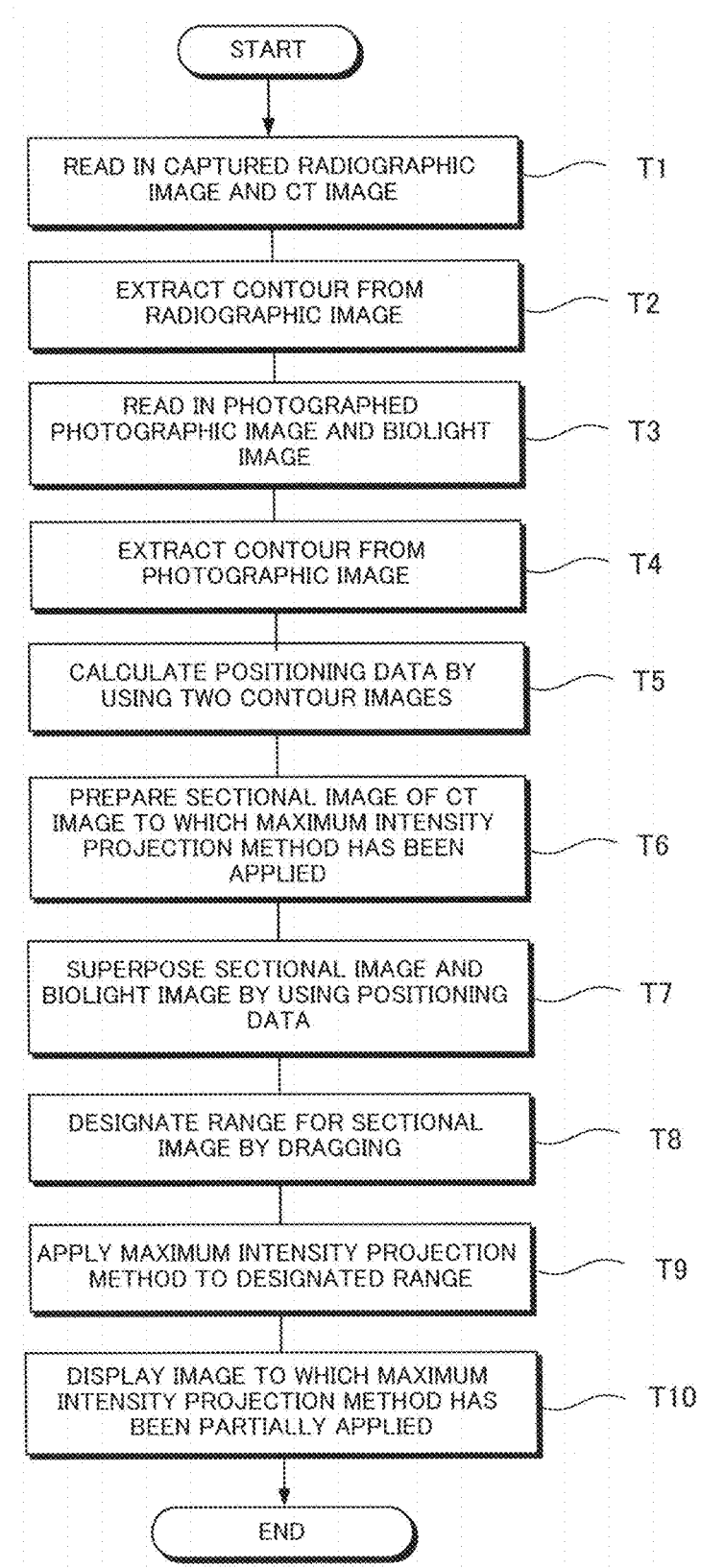
FIG. 10 is a flowchart illustrating one example of an operation of an image processing apparatus according to a second embodiment.

FIG. 10 is a flowchart illustrating one example of an operation of the image processing apparatus 100. Steps T1 to T5 are the same as steps S1 to S5 in the first embodiment and the position adjustment data is calculated by using two contour images. Next, sectional image data obtained by applying the maximum intensity projection method to the three-dimensional X-ray CT image data is prepared (step T6). Then, the sectional image data and the two-dimensional biolight image data are mutually superposed by using the position adjustment data (step T7).

[Working Example]

Figure 11:
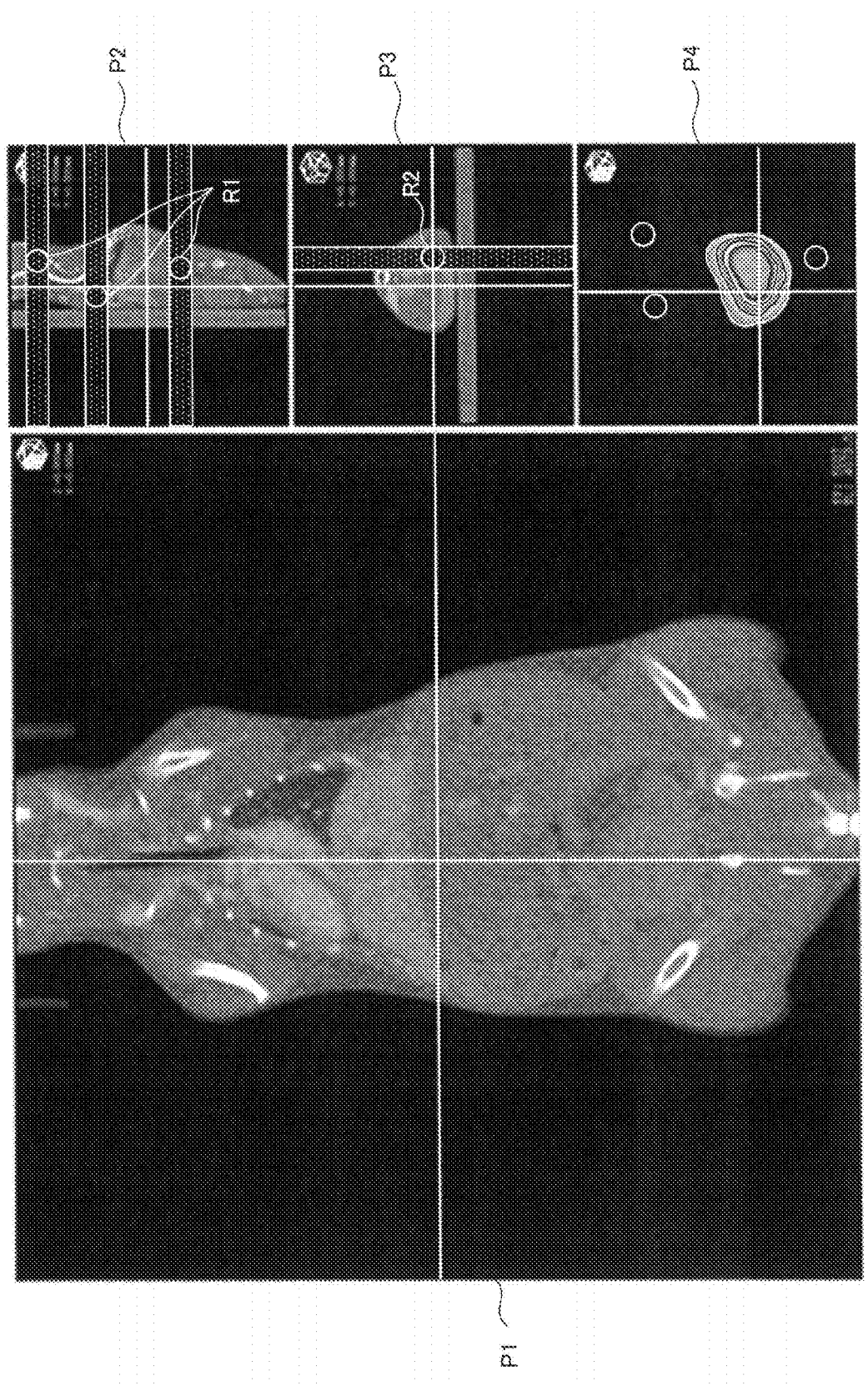
FIG. 11 is a diagram illustrating a screen after having been subjected to superposition processing.

Next, screen display when the process of superposing the images has been actually performed will be described. FIG. 11 is a diagram illustrating a screen obtained after the process of superposing the images has been performed. In FIG. 11, images P1 to P4 respectively represent a coronal section, a sagittal section, a body axis section and a fluorescent image surface of the subject. In the example illustrated in FIG. 11, a circular range R1 is designated by the pointing device such as the mouse on the top right sagittal section P2 of the superposed image. In addition, a circular range R2 is designated on the middle right body axis section P3 of the superposed image.

Figure 12:
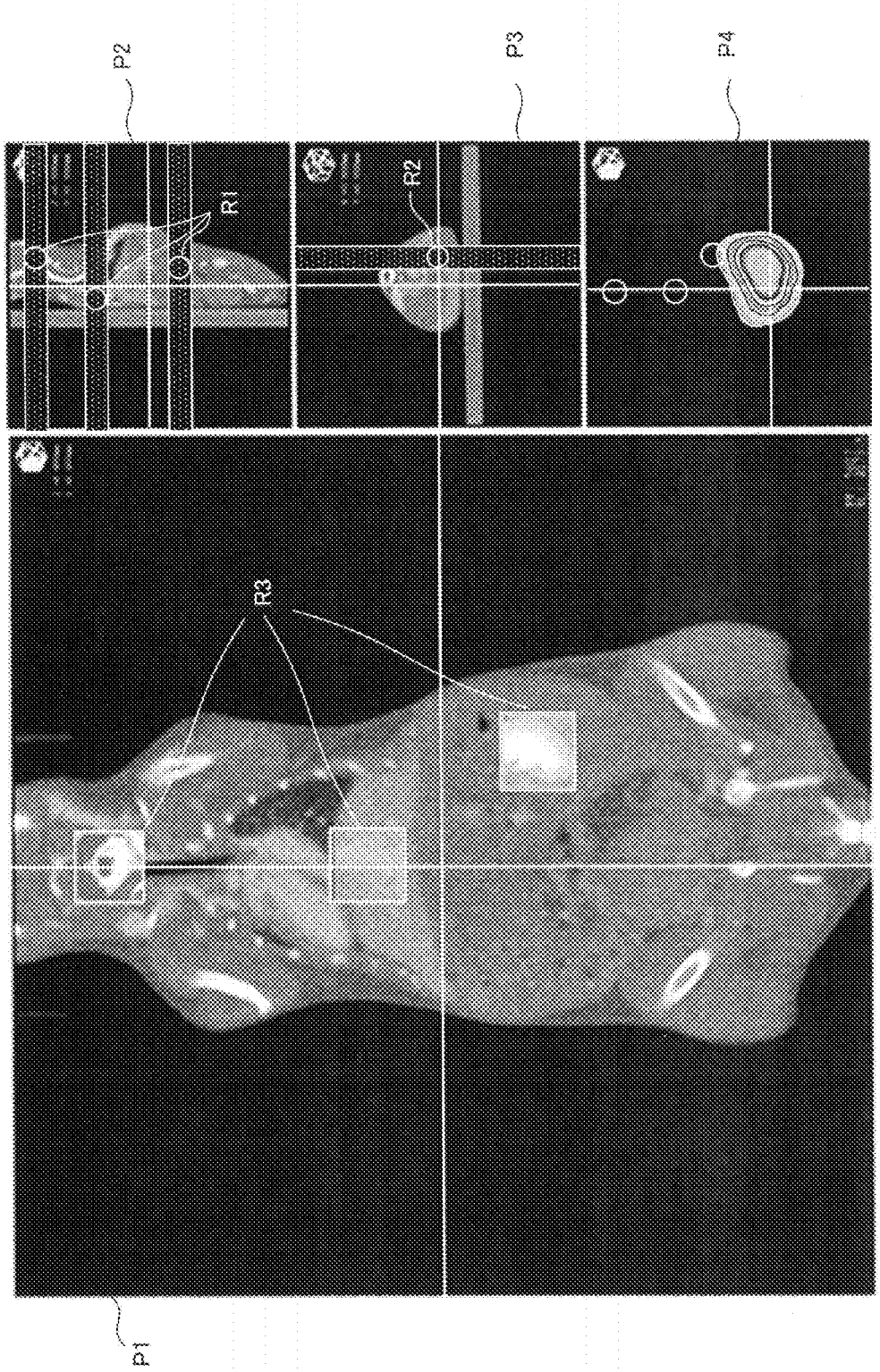
FIG. 12 is a diagram illustrating a screen after having been subjected to processing that the maximum intensity projection method has been applied to a designated range.

FIG. 12 is a diagram illustrating the image of the coronal section obtained after a process of applying the maximum intensity projection method to the three-dimensional X-ray CT image for the designated range has been performed. The image of the coronal section is displayed by locally applying the maximum intensity projection method to the ranges R1 and R2 which have been designated as described above.

Figure 13:
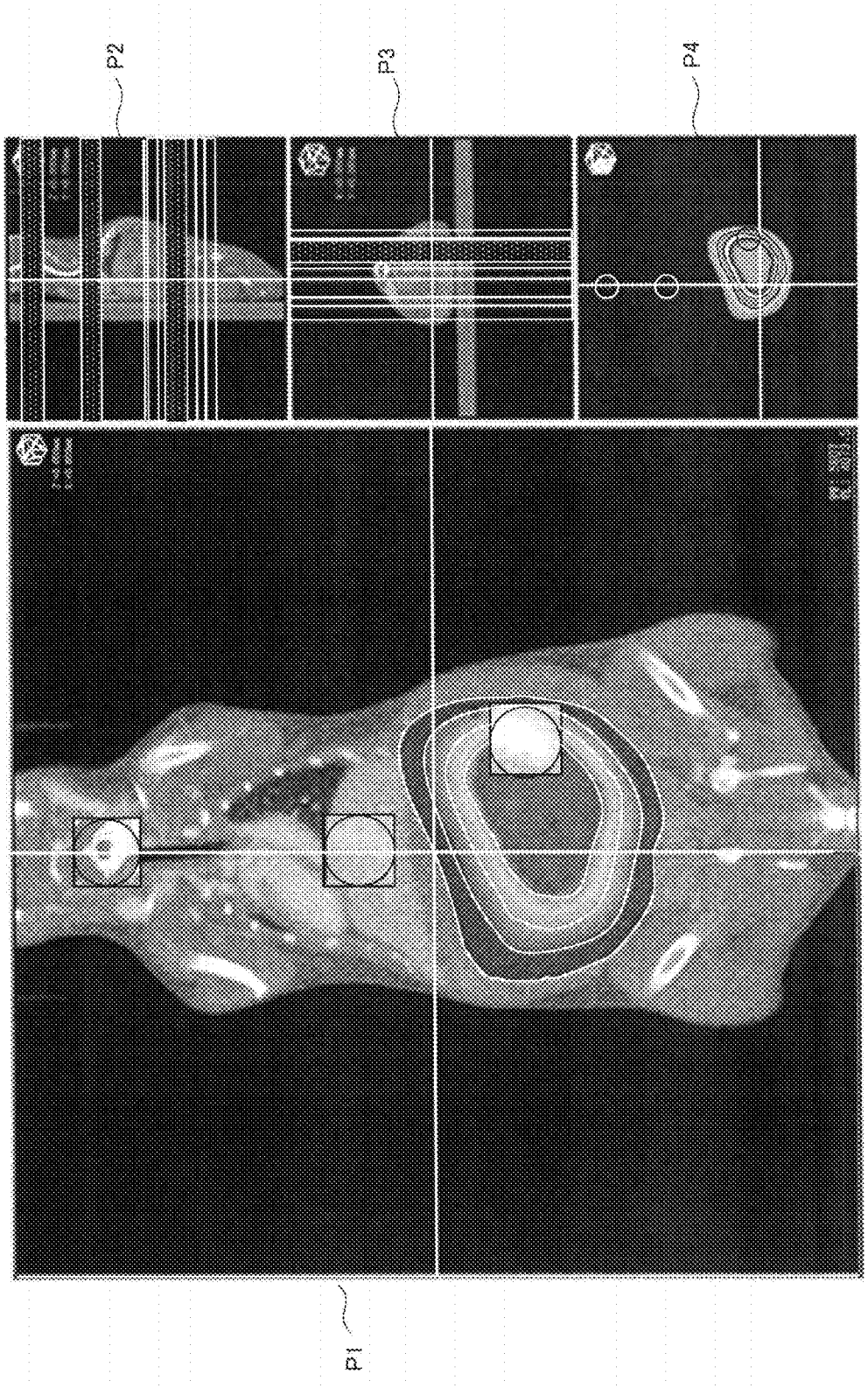
FIG. 13 is a diagram illustrating a synthetic image obtained after fine positioning for matching has been performed.

FIG. 13 is a diagram illustrating a synthetic image obtained after fine positioning has been performed for matching. The synthetic image obtained by synthesizing the two-dimensional fluorescent image with the CT sectional image to which the maximum intensity projection method has been applied for the partial ranges is displayed. The lesion part is emphasized and is clearly displayed.

DESCRIPTION OF REFERENCE SIGNS 50 measurement apparatus
61 gantry
62 control unit
63 rotating arm
64 stage
65 X-ray tube
66 two-dimensional detector
67 arm rotation motor
72 objective lens system
74 light source
74a filter
76 camera
78 dichroic mirror
100 image processing apparatus
105 three-dimensional data reconfiguration unit
110 image data accumulation unit
120 biolight image data accumulation unit
130 calculation unit
140 sectional image generation unit
150 display processing unit
160 operation unit
201 radiographic image
202 contour image
211 photographic image
212 contour image
231 image data
241 biolight image data
251 sectional image
262, 263 fluorescence
270 subject
272 range
273 section
274, 275 abnormal part
R1, R2 range
M subject

What is claimed is:

1. An image processing apparatus used to specify an abnormal part of a subject, the image processing apparatus including one or more processors which execute a program to:
calculate position adjustment data used for matching an X-ray radiographic image of a prescribed position of a specific object and a photographic image of the prescribed position of the specific object obtained by photographing the specific subject, the position adjustment data being calculated by:
extracting, from the X-ray radiographic image, a contour of the prescribed position of the specific object;
extracting, from the photographic image, a contour of the prescribed position of the specific object; and
calculating the position adjustment data based on the extracted contour of the X-ray radiographic image and the extracted contour of the photographic image, and
superpose the X-ray radiographic image and the photographic image based on the calculated position adjustment data; and
display a three-dimensional X-ray CT image which has been correlated with the X-ray radiographic image and a two-dimensional biolight image which has been correlated with the photographic image in superposition,
wherein the one or more processors further executes the program to:
generate a sectional image of the three-dimensional X-ray CT image on a plane which is parallel with a light receiving face of the two-dimensional biolight image, and
generate the sectional image of the three-dimensional X-ray CT image by applying a maximum intensity projection method to the three-dimensional X-ray CT image within a predetermined range in a direction vertical to the light receiving face of the two-dimensional biolight image.

2. The image processing apparatus according to claim 1, wherein the one or more processors further execute the program to:
receive an operation of specifying a range on the sectional image from a user, and
generate the sectional image of the three-dimensional X-ray CT image by applying the maximum intensity projection method to the three-dimensional X-ray CT image for the specified range in the direction vertical to the light receiving face of the two-dimensional biolight image.

3. An image processing apparatus used to specify an abnormal part of a subject, the image processing apparatus including one or more processors which execute a program to:
calculate position adjustment data used for matching an X-ray radiographic image of a prescribed position of a specific object and a photographic image of the prescribed position of the specific object obtained by photographing the specific subject, the position adjustment data being calculated by:
  extracting, from the X-ray radiographic image, a contour of the prescribed position of the specific object;
  extracting, from the photographic image, a contour of the prescribed position of the specific object; and
  calculating the position adjustment data based on the extracted contour of the X-ray radiographic image and the extracted contour of the photographic image, and
superpose the X-ray radiographic image and the photographic image based on the calculated position adjustment data; and
display a three-dimensional X-ray CT image which has been correlated with the X-ray radiographic image and a two-dimensional biolight image which has been correlated with the photographic image in superposition,
wherein the one or more processors further execute the program to:
calculate a rate of magnification from a ratio in pixel size between the contour data of the X-ray radiographic image and the contour data of the photographic image as the position adjustment data between the contour data, and
adjust the size between the contour data by using the rate of magnification and thereafter calculates relative positions on a plane and an angle of rotation around a specific axis of the contour data of the X-ray radiographic image and the contour data of the photographic image, as the position adjustment data between the contour data, such that a correlation value between the contour data satisfies a predetermined condition.

4. An image processing method executed by a computer and used to specify an abnormal part of a test subject, the computer including one or more processors which execute a program to:
calculate position adjustment data for matching an X-ray radiographic image of a prescribed position of a specific object and a photographic image of the prescribed position of the specific object obtained by photographing the specific subject, the position adjustment data calculating step including:
  extracting, from the X-ray radiographic image, a contour of the specific object;
  extracting, from the photographic image, a contour of the specific object; and
  calculating the position adjustment data based on the extracted contour of the X-ray radiographic image and the extracted contour of the photographic image, and
superpose the X-ray radiographic image and the photographic image based on the calculated position adjustment data; and
display a three-dimensional X-ray CT image which has been correlated with the X-ray radiographic image and a two-dimensional biolight image which has been correlated with the photographic image in superposition,
wherein the one or more processors which execute a program to:
generate a sectional image of the three-dimensional X-ray CT image on a plane which is parallel with a light receiving face of the two-dimensional biolight image, and
generate the sectional image of the three-dimensional X-ray CT image by applying a maximum intensity projection method to the three-dimensional X-ray CT image within a predetermined range in a direction vertical to the light receiving face of the two-dimensional biolight image.

5. The image processing method according to claim 4, wherein the computer includes the one or more processors which further executes the program to:
receive an operation of specifying a range on the sectional image from a user, and
generate the sectional image of the three-dimensional X-ray CT image by applying the maximum intensity projection method to the three-dimensional X-ray CT image for the specified range in the direction vertical to the light receiving face of the two-dimensional biolight image.

* * * * *